United States Patent [19]

Ireland

[11] Patent Number: 5,033,319
[45] Date of Patent: Jul. 23, 1991

[54] FILTERING AND SENSING ASSEMBLY AND SYSTEM

[76] Inventor: Oliver L. Ireland, 3 Kingsley Terrace, Kelmscott, Western Australia, Australia, 6111

[21] Appl. No.: 455,426
[22] PCT Filed: Jan. 22, 1988
[86] PCT No.: PCT/AU88/00014
§ 371 Date: Dec. 12, 1989
§ 102(e) Date: Dec. 12, 1989
[87] PCT Pub. No.: WO89/00072
PCT Pub. Date: Jan. 12, 1989

[30] Foreign Application Priority Data

Jul. 3, 1987 [AU] Australia ................. PI 2931

[51] Int. Cl.$^5$ .............................. G01N 1/00
[52] U.S. Cl. ................. 73/863.23; 73/864.81
[58] Field of Search ........... 73/863.23, 863.24, 863.25, 73/863.83, 863.85, 864.34, 864.81, 866.5; 204/433, 264, 276; 436/49, 54

[56] References Cited

U.S. PATENT DOCUMENTS 4,112,768 9/1978 Holland et al. .............. 73/863.24
4,501,161 2/1985 Endo et al. .................. 73/863.25

FOREIGN PATENT DOCUMENTS 0174417 3/1986 European Pat. Off. ......... 73/863.85
1170309 7/1985 U.S.S.R. .................. 73/863.24

Primary Examiner—Robert Raevis
Attorney, Agent, or Firm—Harness, Dickey & Pierce

[57] ABSTRACT

A filtrate evacuation system for obtaining a solids free filtrate from a slurry. The system comprises a filter assembly (11), a detachable filter cup (17), and an extractor tube (14) which is connected to a pump (15). The cup (17) is threadedly attached to a mounting sleeve (16) to define an inner chamber (32). One end of the extractor tube (14) communicates with chamber (32) through the mounting sleeve (16), and the other end communicates with the pump (15) so that filtrate residing within the chamber may be evacuated. The cup (17) is formed of porous filtering material such as sintered metal to provide a solids free filtrate within the chamber (32). By continuously evacuating filtrate from the chamber (32), a sensing probe (12) disposed within the chamber (32) may obtain a real time measurement of a condition of the slurry.

12 Claims, 5 Drawing Sheets

FILTERING AND SENSING ASSEMBLY AND SYSTEM

TECHNICAL FIELD

THIS INVENTION relates to a filtering and sensing assembly and system for continuously obtaining a solids free filtrate from a slurry or solids loaded liquid process, which shall hereinafter be generally referred to as a "slurry", and obtain a real time process measurement thereof. Moreover, the invention enables a continuous filtrate sample to be obtained from a slurry which is constantly representative of conditions within the slurry and provides for appropriate sensing and measurement of such conditions.

BACKGROUND ART

In certain industrial processes, it is necessary to obtain a particular measurement of a condition within a slurry flow, for example the pH level, using precision instruments. In order to obtain an accurate measurement it is necessary to extract a clean solids free liquid from the slurry, on which relevant measurements can be performed.

With previously existing systems for such measurements, much time is usually taken in obtaining the often clean solids free liquid from the slurry material before a measurement can be taken. Hence by the time the actual sensing is performed on the solids free liquid, the measurement obtained is often times no longer representative of the existing condition of the slurry.

Additionally, in controlling such industrial processes, it is desirable to provide a continuous measurement of a condition of the slurry, so that adjustments can be made to the introduction of condition altering additives or the like to the slurry. A problem with systems currently adopted for this continuous measurement is that once a quantity of clean solids free liquid is obtained, it has been difficult to continuously replace the obtained liquid with a constantly representative sample of liquid reflecting the existing conditions of the slurry.

DISCLOSURE OF INVENTION

It is an object of the present invention to provide a filtering and sensing assembly and system which can continuously obtain a solids free filtrate from a passing slurry, which filtrate is relatively closely representative of a particular condition of the slurry.

It is a further object of the invention to provide a filtering and sensing assembly which can be located in a passing slurry to obtain a real time process measurement of the slurry.

In accordance with one aspect of the present invention, there is provided a filtering and sensing assembly for obtaining a real time process measurement of a slurry comprising:

a mounting assembly for location within said slurry; a filter member detachably mounted upon said mounting assembly for contacting said slurry and combining with said mounting assembly to define an enclosed inner chamber for receiving a solids-free filtrate filtered from said slurry;

a passage provided within said assembly for communicating at one end with said inner chamber and at the other end to a pump means to continuously extract said solids free filtrate from said inner chamber; and a sensor probe for sensing a condition of said slurry mounted within said mounting assembly such that the sensor head of said sensor probe reposes within said inner chamber to contact said solids free filtrate prior to extraction through said passage;

wherein said member comprises a porous filtering material through which liquid Within said slurry can continuously filter to situate within said inner chamber said solids free filtrate.

Preferably, the filter member is in the form of a cup having: an open end adapted to be detachably mounted to a complementary connecting portion of said mounting assembly, a base opposite said open end, and a generally annular wall portion comprising said porous filtering material; said cup being disposed for immersion within said slurry such that the outer surface of said annular wall portion is exposed to said slurry.

A filtering and sensing assembly for obtaining a real time process measurement of a slurry comprising:

a mounting assembly for location within said slurry;

filter member detachably mounted upon said mounting assembly for contacting said slurry and combining with said assembly to define an enclosed inner chamber for receiving a solids free filtrate filtered from said slurry;

a passage provided within said assembly for communicating at one end with said inner chamber and at the other end to a pump means continuously extract said solids free filtrate from said inner chamber;

a sensor probe for sensing a condition of said slurry within said mounting assembly such that the sensor head of said probe reposes within said inner chamber to contact said solids free filtrate prior to extraction through said passageway; and wherein said member comprises a persons filtering material through which liquid within said slurry can continuously filter to situate within said inner chamber said solids free filtrate.

BRIEF DESCRIPTION OF DRAWINGS

The invention will be better understood in the light of the following description of several embodiments thereof. The description is made with reference to the accompanying drawings wherein.

DETAILED DESCRIPTION OF EMBODIMENTS

The first embodiment is directed towards a filtering and sensing assembly and system for continuously obtaining a solids free filtrate from a slurry contained in an open vessel, whereby the filtrate provides a representative condition of the slurry such as its pH level, which can be measured, and providing for a real time process measurement of such representative condition.

Figure 1A:
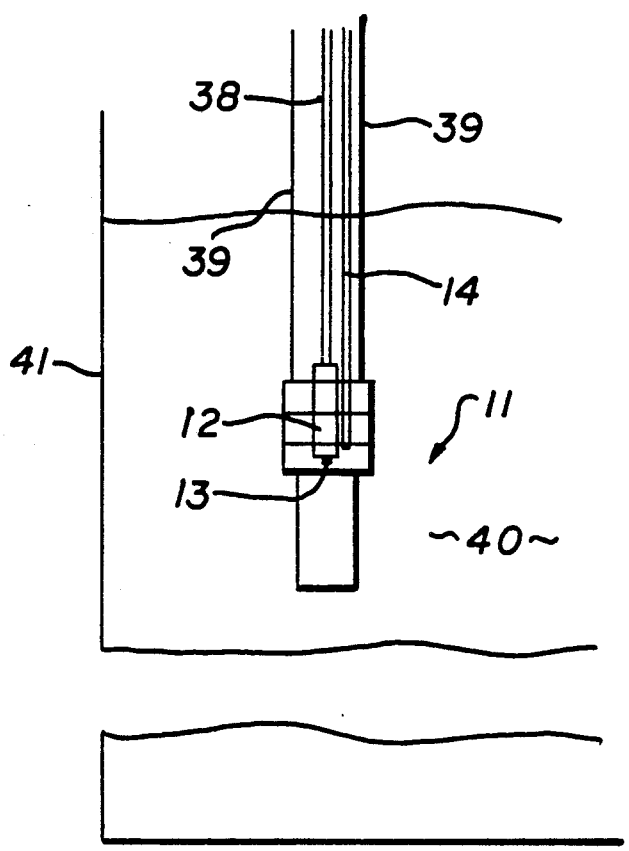
FIG. 1A is a schematic drawing showing the filtering and sensing assembly arranged for use with a slurry contained in an open vessel, in accordance with the first embodiment.
Figure 2:
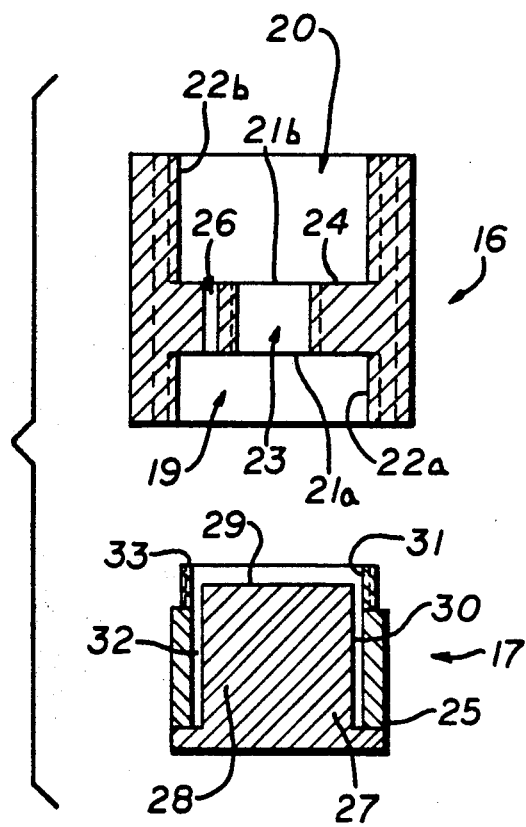
FIG. 2 is an exploded sectional view of the mounting assembly and filter member as described in the first embodiment.
Figure 4:
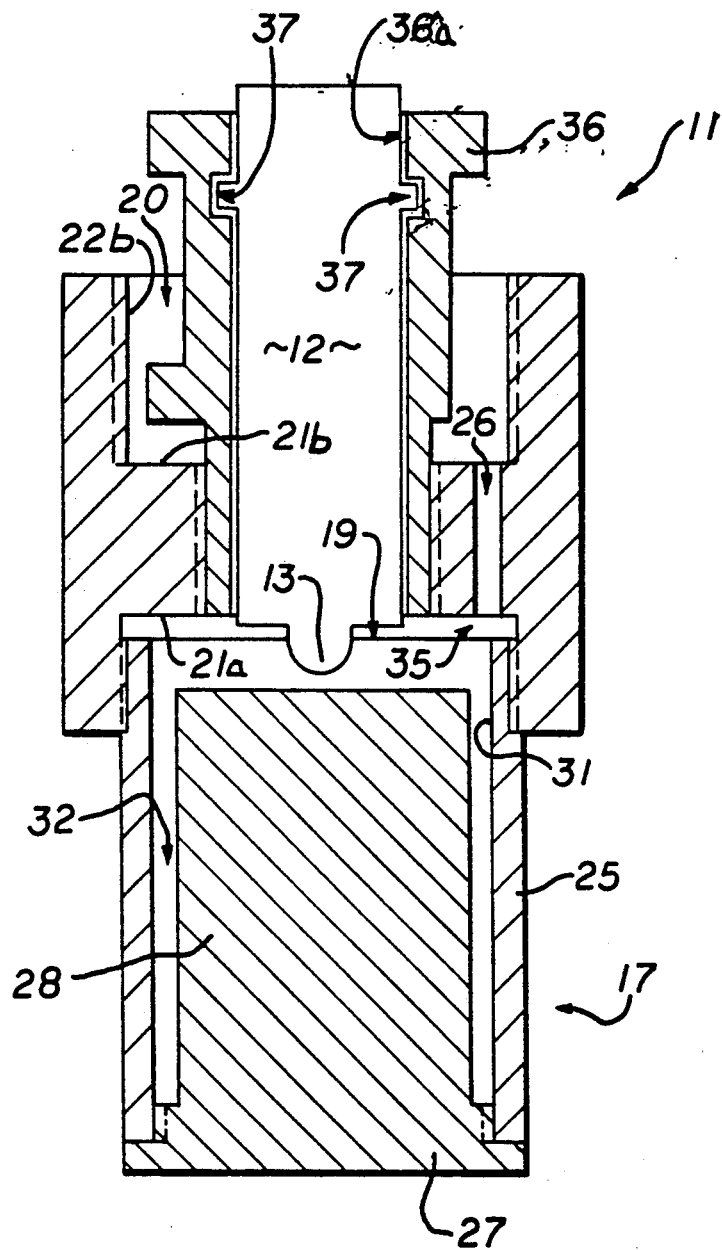
FIG. 4 is a sectional side elevation of the filtering and sensing assembly showing the mounting member connected to the filter assembly and having a probe receptor and sensor probe connected thereto, as described in the first embodiment.

As shown at FIGS. 1A, 2 and 4 of the drawings, the filtering and sensing assembly 11 comprises a mounting assembly and filter member to which is connected a sensor probe 12 having a sensor head 13 disposed within the filter member, and an extractor tube 14 connected at one end to the filter assembly, and at the other end to a pump means 15 to form the filtering and sensing system. The mounting assembly generally comprises a mounting sleeve 16 formed with connecting portions at either axial end and the filter member comprises a cup 17 formed of porous filtering material.

The mounting sleeve 16 is formed of suitable metal or plastics material and is of a diameter larger than the other components of the filtering and sensing assembly. The connecting portions of the sleeve comprise sockets 19 and 20 each having an inner terminal base 21a and 21b and a threaded axial side wall 22a and 22b. The socket 19 allows threaded connection of the mounting sleeve to a complementary threaded end of the cup 17 and the socket 20 allows threaded connection to an assembly supporting tube, to be described in more detail later. The sleeve 16 also has an inner axial bore 23, which extends from the base 21a of the socket 19 to the base 21b of the other socket 20, and is itself internally threaded to accommodate a probe receptor 36 for locating the sensor probe 12 within the sleeve. The bore is constricted relative to the sockets 19 and 20 by means of an annular shoulder 24 which extends radially inwardly of the sleeve between the sockets. The shoulder is symmetrically arranged so as to ensure the central axis of the bore 23 is co-axial with the central axis of the sleeve 16. Consequently, the shoulder locates the probe receptor centrally within the sleeve, and maintains it in spaced relationship with the side walls 22a and 22b of the sockets. The shoulder 24 is of sufficient radial extent to incorporate an aperture 26 therein which extends between opposite axial sides of the shoulder so as to communicate with the sockets 19 and 20 at its opposite ends. The aperture 26 receives the extractor tube 14 and radially disposes the same between a constricted portion of the bore and the side walls 22a and 22b of the sockets.

The cup 17 essentially comprises an annular wall portion 25 formed of porous filtering material, an open terminating portion 33 at one axial end of the wall portion and a closed base portion comprising a filtrate impervious plug 27 at the other axial end. The terminating portion 33 is externally threaded to permit detachable mounting of the cup to the socket 19. The porous filtering material for the annular wall 25 is preferably of sintered metal or similar fine filtering material. The porosity of the filtering material may be selected to suit the particular slurry and condition thereof to be measured. The plug 27 is threaded to the other end of the annular wall portion 25, and is provided with an inner spigot portion 28 formed of filtrate impervious material which extends from the base of the cup to a distal end 29 axially spaced from the open end of the cup. The spigot portion 28 is formed with an axially extending side wall 30 which is generally spaced from the inner face 31 of the annular wall portion 25 to define a chamber 32 within the remainder of the cup. Consequently, the provision of the spigot portion 28 reduces the volume of the chamber 32 relative to the total internal volume of the cup minus the spigot portion, and maintains the chamber co-extensive with the inner face 31 of the annular wall portion to provide for the flow of filtrate from the inner face to the open end of the cup.

The axial extent of the threaded portion of the cup 17 is less than axial extent of the side wall 22a of the socket 19 and thus when the cup is connected to the mounting sleeve, the terminating portion 33 of the open end of the cup is spaced axially from the base 21a of the socket 19 to define an annular groove 35 therebetween. The annular groove 35 communicates with the corresponding end of the aperture 26 to allow unrestricted flow of fluid from the chamber 32 of the cup to the extractor tube 14, and vice versa.

As previously described the annular shoulder 24 of the mounting sleeve 16 is internally threaded to allow the probe receptor 36 to be connected thereto, permitting the sensor probe 12 to be centrally disposed within the mounting sleeve with the sensor head 13 thereof communicating with the chamber 32 opposite the end 29 of the spigot portion 28. In the case of the sensor probe itself being directly connected to the shoulder, the diameter of the probe corresponds to the diameter of the bore 23 and has an outer surface which is complementarily threaded to the internal surface of the bore to allow a screw connection of the probe to the sleeve. In such an arrangement, a radial flange (not shown) is provided upon the outer periphery of the sensor probe which is intended to abut against the side of the shoulder 24 which forms the base 21 of the socket 20 upon obtaining the correct axial depth of the sensor head 13 within the chamber 32. This correct axial depth accords to a position of the sensor head within the confines of the cup 17.

By the interconnection of the aforementioned components, the inner chamber 32 is entirely enclosed and can be disposed within the slurry.

In cases where the sensor probe is not of a standard size to directly connect to the bore of the mounting sleeve as shown in the drawings, the probe receptor 36 is used which is in the form of an elongate sleeve having an external diameter corresponding to the internal diameter of the constricted bore and has a portion of its outer periphery complementarily threaded to the bore to permit screwed connection therebetween. The probe receptor 12 furthermore is provided with an axial bore 36a of a diameter corresponding to the diameter of the sensor probe and through which the probe may be inserted and retained. In the present embodiment, the probe receptor is formed with a groove 37 proximate its outer end which is shaped to provide a twist lock connection for probes which employ a bayonet cap connector. It should be appreciated, however, the design of the probe receptor may be altered to provide a screw type connection for probes employing a screw type of connector.

The extractor tube 14 comprises a stainless steel collar (not shown) fitted upon one end of a plastic tube which provides a passage for the flow of filtrate therealong. The collar has a diameter commensurate to that of the aperture 26 so that it may be inserted into the aperture 26 and be frictionally and sealingly disposed therein to allow for the continual flow of filtrate along the passage thereof to or from the chamber 32. The collar is retained within the aperture and is prevented from axial movement therefrom by having its end within the annular groove 35 swagged. The other end of the plastic tube is adapted for connection to the pump means 15 by a flow reversing means to form the filtering and sensing system.

The intermediate portion of the extractor tube 14 and the leads 38 of the probe and sensor are protected within a filter assembly supporting tube 39, as shown at FIG. 1A of the drawings. The end of the supporting tube 39 is externally threaded to complement the internal thread of the socket 20 and is of an external diameter which corresponds to the internal diameter of the socket to allow threaded connection therebetween. Consequently, the filtering and sensing assembly 11 when attached to the end of the supporting tube 39 can be supported within the slurry 40 of the vessel 41 by means of the supporting tube. Thus, the supporting tube provides the dual function of supporting the filtering and sensing assembly 11 and also protecting the extractor tube 14 and leads 38 of the sensor probe from the surrounding slurry when immersed therein.

Figure 6:
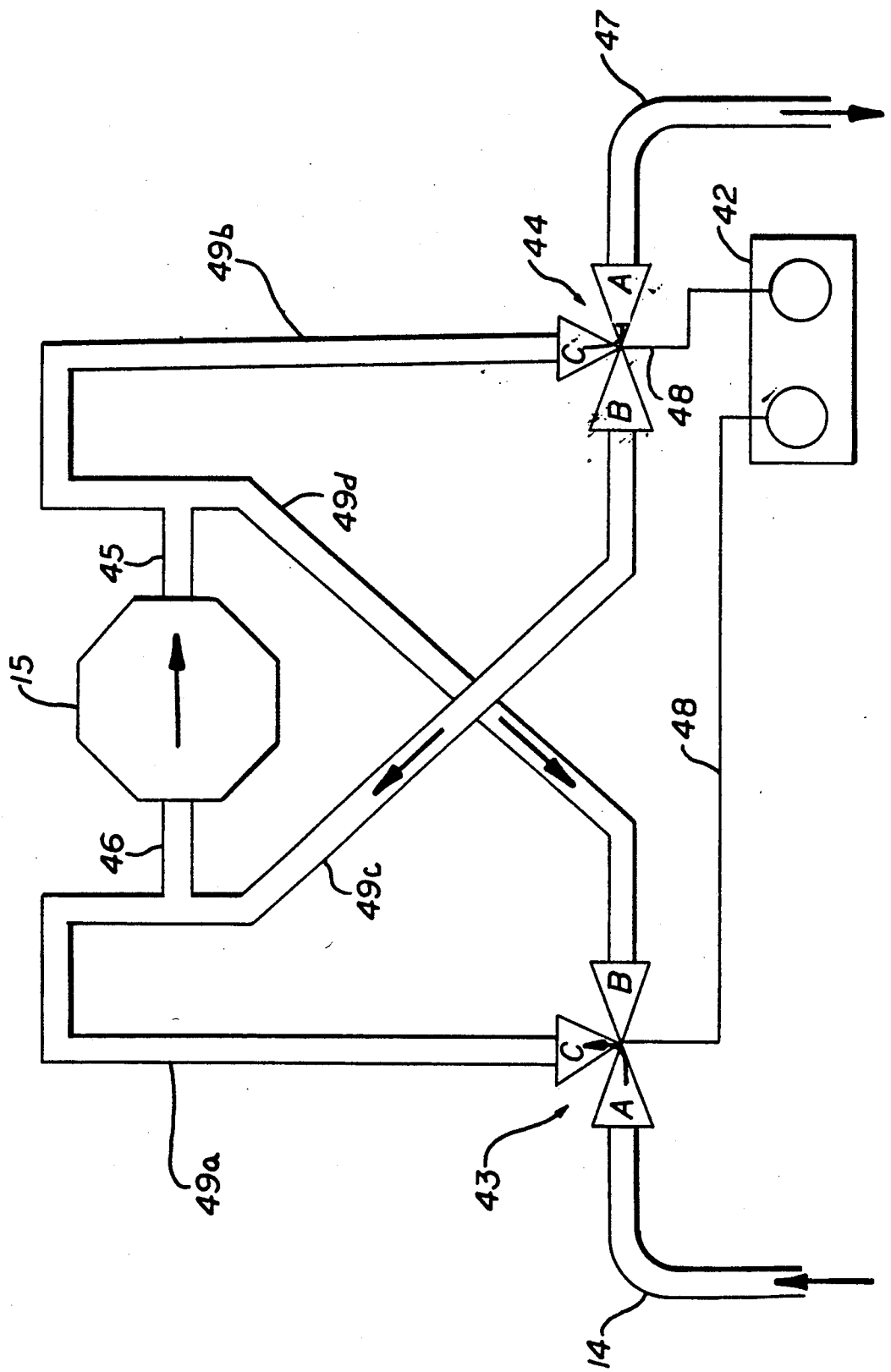
FIG. 6 is a schematic diagram of the flow reversing means used with the filtering and sensing assembly of the first embodiment.

The flow reversing means is best illustrated at FIG. 6 of the drawings and essentially comprises valve means connected between the inlet and outlet ports of the pump means 15 and control means 42 which selectively switches the valve means.

In the present embodiment, the valve means comprises a pair of three way solenoid valves 43 and 44. Each solenoid valve has a common port A through which fluid may flow in either direction, and two switchable ports B and C respectively, which may be alternately switched from one to the other to allow fluid flow through the selected port and impede fluid flow through the other.

The valves are arranged so that the first valve 43 has the common port A thereof connected to the other end of the extractor tube 14 and the other two switchable ports B and C are respectively connected to the outlet port 45 and an inlet port 46 of the pump means. The second valve 44 has its common port A connected to a filtrate discharge reservoir (not shown) via an interconnecting discharge tube 47, or simply to a sufficient length of discharge tube 47, which itself may constitute the filtrate discharge reservoir. The other two switchable ports B and C are respectively connected to the inlet port 46 and outlet port 45 of the pump means 15. The control means 42 has electrical connectors 48 connected to the respective control terminals of the solenoid valves to provide electrical signals thereto for switching the solenoids within the valves. In the normally closed arrangement of the solenoid valves, the switchable port C is selected to allow fluid flow from the extractor tube 14 through the common port A and the switchable port C, along the interconnecting tube 49A to the input port 46 of the pump means and subsequently from the pump means through the outlet port 45 thereof along the interconnecting tube 49B, through the switchable port C and common port A of the second valve 44, and to the discharge tube 47.

The pump means 15 is of the vacuum type and hence in the aforementioned selection of the valve means, operates to evacuate filtrate received within the chamber 32 by creating a pressure differential which induces the passage of further liquid through the walls of the filter member to replace the extracted filtrate. The extracted filtrate is ultimately discharged to the discharge tube 47 and so to the discharge reservoir. Accordingly, a constant flow of liquid from the slurry into filtrate for measurement and extraction from the chamber 32 is created, enabling continuous measuring of the liquid condition to be performed, whereby the liquid is continuously representative of the existing condition of the slurry flowing past the filter assembly.

The flow reversing means is activated when the control means energises the solenoid valves so as to select the switchable ports B. In this mode, liquid previously discharged is extracted from the discharge tube or reservoir through the common port A and switchable port B of the second valve 44 and along the interconnecting tube 49C to the input port 46 of the pump means. The liquid is then pumped out through the outlet port 45 of the pump means along the interconnecting tube 49D to the first valve 43, through the switchable port B and common port A thereof and along the extractor tube 14 to enter the chamber 32. Thus, the flow reversing means utilises the pump means 15 to create a pressure differential reversal, whereby filtrate previously extracted from the chamber can be returned to the chamber under pressure causing the filtrate within the chamber to be flushed through the walls of the filter member thus any blockage or blinding upon the external face of the cup, which is usually caused by the build up of solids upon the cup pursuant to filtering liquid therefrom may be cleared.

The control means includes a control circuit which provides switching signals to energise and de-energise the solenoid valves alternately and in perpetuity. Thus after the control circuit produces a switching signal to energise the solenoids and select the switchable port B of both valves, the control circuit subsequently produces another switching signal which de-energises the solenoids of the valves and selects the switchable port C of both valves and then repeats this cycle of operation. The control means also includes a timing means to determine the time period between switching of the valve means, so that the operation of the flow reversing means and the filtering system can be tuned to suit the particular requirements of the slurry measurement being undertaken.

It should be noted that a particular advantage of the present embodiment is that by having a chamber of reduced volume, the ability of the system to obtain a real time measurement of the condition of the slurry is greatly enhanced whereby due to the low volume of filtrate situated within the cup, the filtrate can be rapidly evacuated from the chamber resulting in a reduced residence time within the cup and allowing the sensor to sense the condition of freshly filtered filtrate continuously.

The second embodiment is directed towards a filtering and sensing assembly substantially similar to that described in the preceding embodiment except that the particular design of the filter member has been slightly modified to increase the surface area of the cup which comprises the porous filtering material and which is exposed to the passing slurry.

Figure 5:
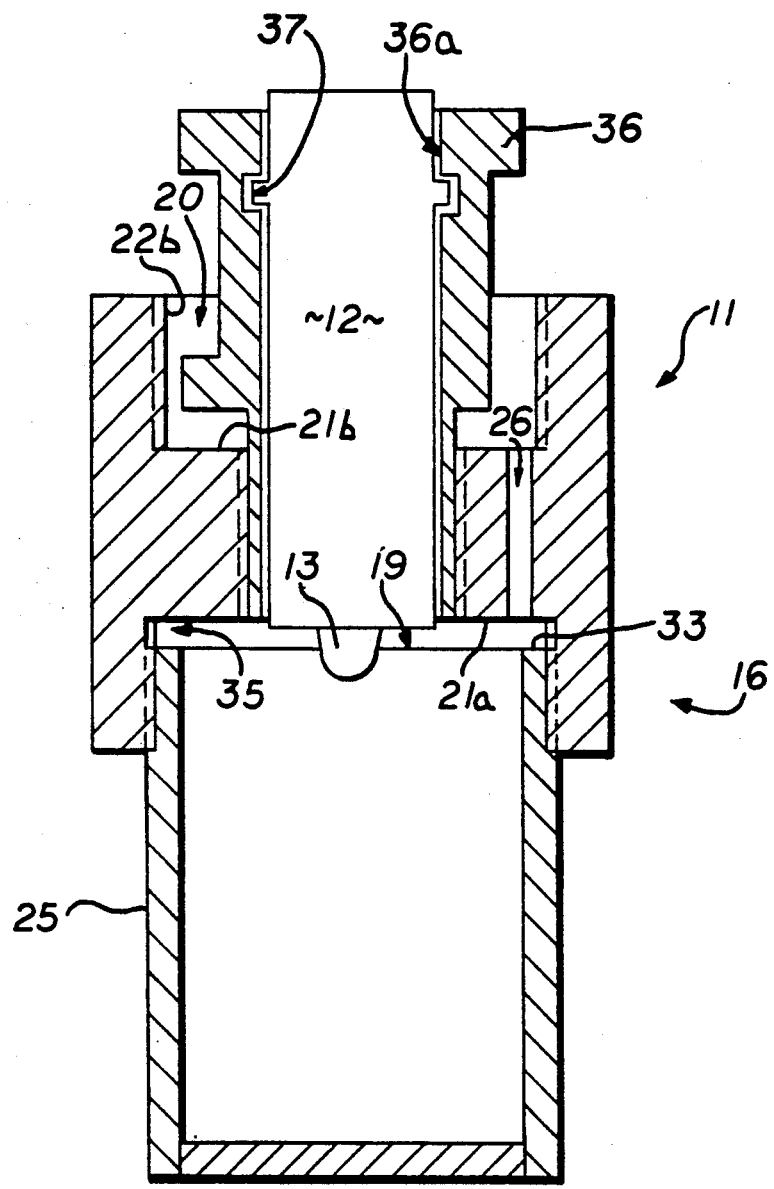
FIG. 5 is a sectional side elevation of the filtering and sensing assembly showing alternative form of filter member connected to the mounting assembly, as described in the second embodiment.

The filtering and sensing assembly of the present embodiment is more clearly shown at FIG. 5 of the drawings, where the same reference numerals as used in the previous embodiment, have been adopted to depict the same components of the assembly employed in both embodiments.

As shown in the drawing, the filter cup 17 has its base 5 formed from the same porous filtering material as is the annular wall portion 25, thereby increasing the surface area of the porous filtering material which may be exposed to the surrounding slurry. In this arrangement the inwardly extending spigot portion is omitted and hence the internal volume of the chamber 32 is commensurate with the total internal volume of the cup.

It should be noted that the omission of the spigot portion extending from the base of the cup described in the previous embodiment has the disadvantage that the residence time of filtrate situated within the confines of the cup is increased and thus reduces the efficiency of the filter assembly in obtaining a real time measurement of the condition of the surrounding slurry due to the increased volume of filtrate which is required to be evacuated from the chamber. Accordingly, the present embodiment only finds utility in measuring slurries where real time sensing is of reduced importance and the viscosity of the filtrate is low.

The third embodiment is directed towards a filtering and sensing assembly and system substantially similar to that described in the first embodiment but which permits filtering and measurement of the condition of the slurry within a closed pipeline.

Figure 1B:
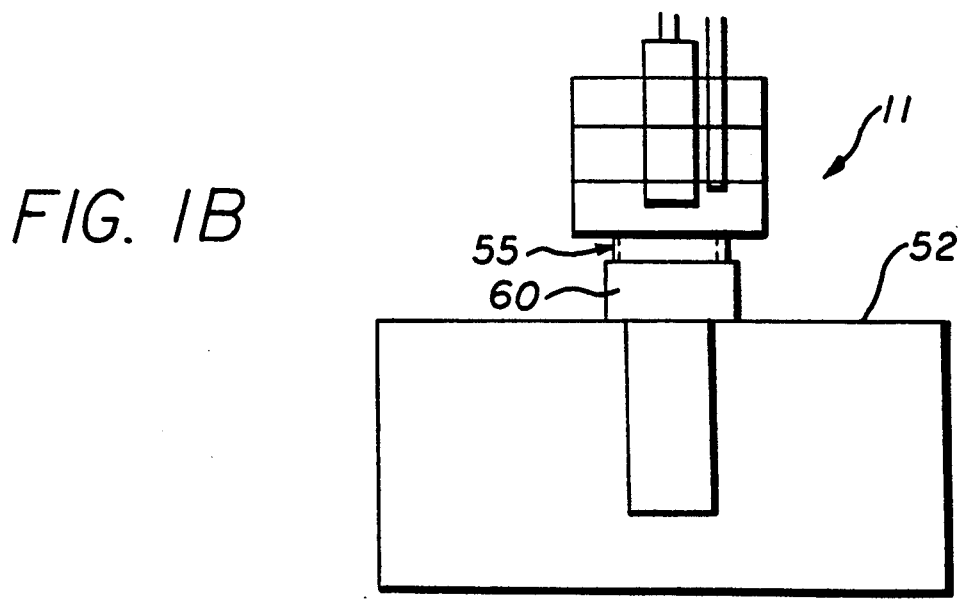
FIG. 1B is a schematic drawing showing a filtering and sensing assembly arranged for use in a slurry flowing through a closed pipeline, in accordance with the third embodiment.
Figure 3:
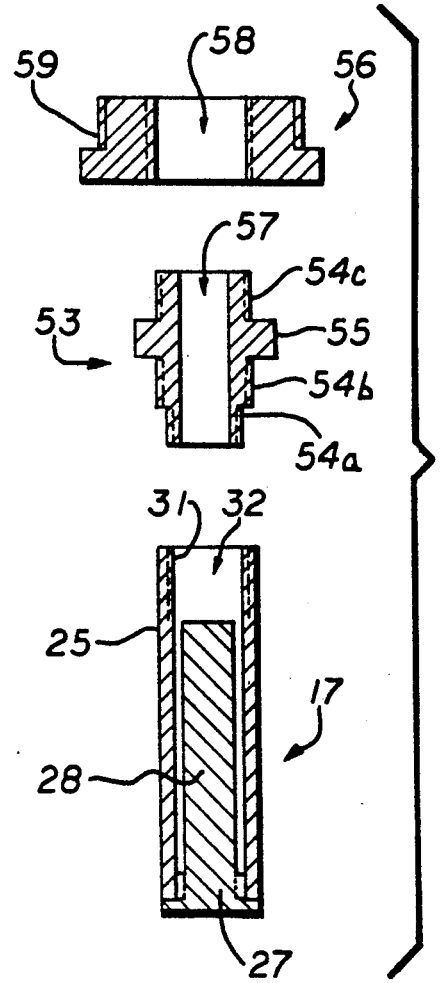
FIG. 3 is an exploded sectional view of the mounting assembly and filter member, as described in the third embodiment.

The filtering and sensing assembly used in the filtering and sensing system of the present embodiment is shown more clearly at FIGS. 1B and 3 of the drawings and accordingly the same reference numerals as used in the previous embodiments which depict similar parts of the assembly have been used in the description of the present embodiment.

As shown at FIG. 1B of the drawings, the filtering and sensing assembly 11 is required to be inserted into an opening provided in a pipeline 52. Therefore, it is necessary to ensure appropriate sealing between the filtering and sensing assembly and the pipeline and secure fastening of the assembly to the pipeline. Both of these objectives are achieved by utilising an end collar 53 which is in the form of a nipple for interconnecting the cup 17 and the mounting sleeve 16 of the assembly, and a threaded socket 60 which is welded to an opening made in the pipeline to enable the collar 53 to be threadedly connected thereto.

As shown at FIG. 3 of the drawings, the cup 17 used in the present embodiment is of a significantly smaller diameter than the cup described in previous embodiments, but otherwise is of similar design to the cup described in the first embodiment. Accordingly, the annular wall 25 and the inwardly extending spigot portion 28 of the cup are much more elongated than their counterparts in the first embodiment. The inner face 31 of the annular wall portion additionally is threaded proximate the outer end thereof to receive a complementary threaded end portion of the collar 53.

The collar 53 is divided up into three discrete axial threaded portions 54A, 54B and 54C. The portion of smallest diameter 54A is disposed at one end of the collar to define the complementary threaded end portion and thus is adapted to be threadedly connected to the outer end 3 of the cup 17. A second intermediate portion 54B of larger diameter than the end portion 54A is disposed adjacent to the end portion 54A, a prescribed distance from the end of the collar. The diameter of this intermediate portion 54B is larger than the external diameter of the cup 17 and is of sufficient threaded axial extent to be threadedly engaged within the threaded socket 60.

The socket 60 is located within an opening of adequate size created by piercing the wall of the pipeline and is sealingly welded to the periphery of the opening to enable communication with the inside of the pipeline through the bore of the socket.

Provided adjacent the intermediate portion 54B is a hexagonal-shaped flange 55 which is again of a larger diameter than the intermediate portion 54B and provides a head which can be clasped for screwing the collar 53 to the threaded socket 60 in its position upon pipeline. Finally, the third axial portion 54C is disposed between the flange portion 55 and the other end of the collar and is intended to be connected to a reducer bush 56 for connection to the socket 19 of the mounting sleeve 16. The collar 53 is provided with an inner bore which extends between the axial ends thereof to extend the chamber 32 between the cup 17 and the mounting sleeve 16. The reducer bush 56 is itself provided with an inner axial bore which is internally threaded to receive the complementary threaded end portion 54C of the collar 55. The reducer bush 56 is formed with an externally threaded end spigot 59 which is of a similar diameter to the internal diameter of the socket 19 and furthermore is complementary threaded thereto to be connected to this end of the mounting sleeve. The axial extent of the spigot end 59 of the reducer bush 56 is less than the axial extent of the side wall 22 of the socket 19 to define the annular chamber 30 proximate the base 21 of the socket.

With the filtering and sensing assembly mounted to the pipeline, the operation of the filtering system of the present embodiment is identical to that of the first embodiment, whereby fluid is evacuated from the chamber by way of the pump means and filtrate flow is reversed for flushing by operation of the flow reversing means.

It should be appreciated that the scope of the present invention is not limited to the particular embodiments herein described. In particular, the filtering and sensing assembly and system is not limited to the particular application herein described, i.e. for measuring a condition of a slurry, and may be used in other applications where it is necessary to continuously obtain a solid free filtrate which is relatively closely representative of the condition of the slurry from which it is extracted.

This invention is not limited to slurry applications, but is intended for use in any liquid process operation requiring liquid analysis.

The claims defining the invention are as follows:

1. A filtering and sensing assembly for obtaining a real time process measurement of a slurry comprising:
   a mounting assembly for location within said slurry; a filter member detachably mounted upon said mounting assembly for contacting said slurry and combining with said mounting assembly to define an enclosed inner chamber for receiving a solids-free filtrate filtered from said slurry;
   a passage for communicating at one end with said inner chamber and at the other end to a pump means to continuously extract said solids free filtrate from said inner chamber; and
   a sensor probe for sensing a condition of said slurry mounted within said mounting assembly such that the sensor head of said sensor probe reposes within said inner chamber to contact said solids free filtrate prior to extraction through said passage;

wherein said member comprises a porous filtering material through which liquid within said slurry can continuously filter to situate within said inner chamber said solids free filtrate.

2. A filtering and sensing assembly system as claimed at claim 1, wherein said filter member is in the form of a cup having: an open end adapted to be detachably mounted to a complementary connecting portion of said assembly, a base opposite said open end, and a generally annular wall portion comprising said porous filtering material; said cup being disposed for immersion within said slurry such that the outer surface of said annular wall portion is exposed to said slurry.

3. A filtering and sensing assembly as claimed at claim 2, wherein said inner chamber is of a reduced volume relative to the total internal volume of said cup and is co-extensive with the inner face of said annular wall portion to provide for the flow of filtrate from said inner face to said one end of the passage.

4. A filtering and sensing assembly system as claimed at claim 3, wherein said filter member includes an inner spigot portion of filtrate impervious material extending from the base of said cup to a point spaced from said open end and having an axially extending side wall generally spaced from the inner face of said annular wall portion of said cup to define said inner chamber of reduced volume therebetween.

5. A filtering and sensing assembly as claimed at claim 2, wherein said mounting assembly includes a mounting sleeve having a socket at one end forming said complementary connecting portion, and an inner axial bore extending from the other end of said sleeve to communicate with the base of said socket, said axial bore being adapted to accommodate said sensor probe such that said sensor head may be disposed within the confines of the side walls and base of said socket so as to communicate with said inner chamber when said filter member is mounted upon said assembly.

6. A filtering and sensing assembly as claimed at claim 5, wherein said sleeve includes an annular shoulder extending radially inwardly of the sleeve to constrict said bore at the base of said socket, said shoulder being provided to locate said sensor probe centrally within said sleeve, and spaced from the side walls of said socket, and said shoulder having an aperture extending between opposite axial ends of said shoulder to locate said passage between the constricted portion of said bore and the side walls of said socket. said bore at the base of said socket, said shoulder being provided to locate said sensor probe centrally within said sleeve, spaced from the side walls of said socket, and incorporate an aperture therein extending between opposite axial ends of said shoulder to dispose said passage between the constricted portion of said bore and the side walls of said socket.

7. A filtering and sensing assembly as claimed at claim 6, wherein the terminating portion of the open end of said cup is spaced axially from the base of said socket when said cup is mounted to said socket to define an annular groove, to allow unrestricted flow of fluid from said inner chamber to said passage or vice versa.

8. A filtering and sensing system for obtaining a real time process measurement of a slurry comprising a filtering and sensing assembly as claimed at claim 1 wherein said passage is connected via a flow reversing means to said pump means for selectively reversing the flow of said filtrate so as to flush said casing.

9. A filtering and sensing system as claimed at claim 8, wherein said flow reversing means comprises valve means connected to the inlet and outlet ports of the pump means for allowing filtrate flow to and from said pump means, and control means for selectively switching said valve means to alternatively direct said filtrate flow through said passage from said chamber or to said inner chamber.

10. A filtering and sensing system as claimed in claim 9, wherein said valve means comprises a pair of three way solenoid valves, the first valve arranged so that the common port thereof is connected to said passage and the other two switchable ports are respectively connected to the inlet and outlet ports of said pump means, and the second valve arranged so that the common port thereof is connected to a filtrate discharge line or reservoir and the other two switchable ports are respectively connected to the inlet and outlet ports of said pump means, and said control means is arranged, when directing filtrate flow through said passage from said inner chamber, to select the switchable port connected to the pump inlet of the first valve and the switchable port connected to the pump outlet of the second valve, and when directing filtrate flow through said passage to said chamber, to select the other switchable ports, thereby reversing filtrate flow.

11. A filtering and measuring system as claimed at claim 9, wherein said control means alternatively switches said valve means to perpetually provide repeated changes in the direction of filtrate flow through said passage and inner chamber.

12. A filtering and measuring system as claimed at claim 9, wherein said control means includes timing means to control the time period between switching of said valve means.

* * * * *

UNITED STATES PATENT AND TRADEMARK OFFICE
CERTIFICATE OF CORRECTION

PATENT NO.  :    5,033,319

DATED       :    July 23, 1991

INVENTOR(S) :    Oliver L. Ireland

It is certified that error appears in the above-identified patent and that said Letters Patent is hereby corrected as shown below:

Column 8, line 54, Claim 1, begin new paragraph with "a" (second occurrence).

Column 9, line 48 through Column 10, line 3, Claim 6, delete "said bore at the base of said socket, said shoulder being provided to locate said sensor probe centrally within said sleeve, spaced from the side walls of said socket, and incorporate an aperture therein extending between opposite axial ends of said shoulder to dispose said passage between the constricted portion of said bore and the side walls of said socket.".

Column 10, line 24, Claim 10, "in" should be --at--.

Signed and Sealed this

Fifteenth Day of June, 1993

Attest:

MICHAEL K. KIRK

*Attesting Officer*          *Acting Commissioner of Patents and Trademarks*